United States Patent [19]

Gabetta et al.

[11] Patent Number: 5,070,212
[45] Date of Patent: Dec. 3, 1991

[54] INTERMEDIATES USEFUL FOR THE SYNTHESIS OF DELPHINIDIN CHLORIDE

[75] Inventors: Bruno Gabetta; Raffaello Giorgi, both of Milan, Italy

[73] Assignee: IdB Holding SpA, Milan, Italy

[21] Appl. No.: 499,054

[22] Filed: Mar. 26, 1990

[30] Foreign Application Priority Data

Mar. 28, 1989 [GB] United Kingdom ............... 8907008

[51] Int. Cl.$^5$ .......................................... C07D 311/62
[52] U.S. Cl. ................................................. 549/399
[58] Field of Search .......................... 549/399; 558/58; 560/109, 254

[56] References Cited

U.S. PATENT DOCUMENTS 3,314,975   4/1967   Jurd ..................................... 549/399

Primary Examiner—Nicky Chan
Attorney, Agent, or Firm—Kirschstein, Ottinger, Israel & Schiffmiller

[57] ABSTRACT

A process is provided for producing delphinidin which comprises reacting a compound of formula

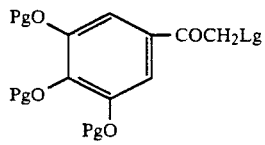

wherein each Pg represents a hydroxyl protecting group, and Lg represents a leaving group with a compound of formula

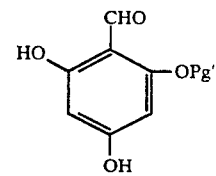

wherein Pg' represents a hydroxyl protecting group characterized in that the compound of formula VII is produced from an intermediate of formula

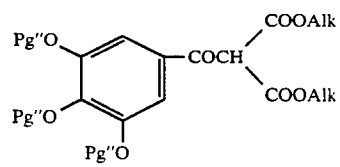

wherein each Pg" represents a hydroxyl protecting group and each Alk represents lower alkyl, by pg,2
(i) subjecting the intermediate of formula IX to hydrolysis and decarboxylation to form 3,4,5-trihydroxyacetophenone of formula

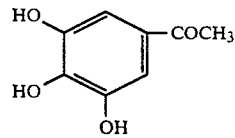

(ii) converting the 3,4,5-trihydroxyacetophenone to the compound of formula VII by introduction of the protecting groups Pg" and converting the group of formula —COCH$_3$ to a group of formula —COCH$_2$Lg.

4 Claims, No Drawings

INTERMEDIATES USEFUL FOR THE SYNTHESIS OF DELPHINIDIN CHLORIDE

This invention relates to a process for synthesising delphinidin and its salts, to a novel group of intermediates formed during the synthesis and to novel procedures for producing the intermediates.

Delphinidin is a member of the class of substances known as anthocyanidins. Its chloride has the following structure

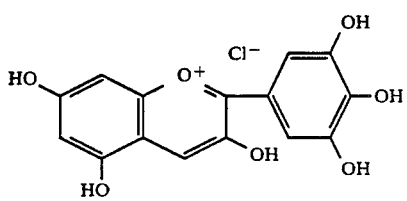

Anthocyanidins are polyphenolic substances which are widely distributed in nature in the form of glycosides known as anthocyanins, and as such are largely responsible for the colouring of fruits and flowers. Anthocyanidins are endowed with remarkable cicatrizing or healing properties and moreover possess anti-inflammatory, vasoprotective, hypolipaemic, hypocholesterolaemic and hypoglycaemic activity. Their pharmaceutical use in these areas has been described and claimed in our earlier patents (GB 1589294 and GB 1595351; Inverni Della Beffa SpA, Milan). Amongst the anthocyanidins, delphinidin is one of the most widespread in nature and pharmacologically most active.

Delphinidin can be obtained by hydrolysis of its glycosidic derivatives, by semi-synthesis from natural substances containing a suitably substituted flavone nucleus, or by complete synthesis by Robinson's method (W. Bradley, R. Robinson and G. Schwarzenbach, J. Chem. Soc., 793, 1930). The known procedure for the complete synthesis of delphinidin is illustrated in Scheme 1. This procedure involves the reaction of triacetylgalloyl chloride (II) with diazomethane. The resulting diazoketone (III) is then transformed by acetolysis into ω-acetoxy-3,4,5-triacetoxyacetophenone (IV), which is condensed with the benzoate (V) in acidic medium to give the protected delphinidin (VI). Delphinidin chloride (I) may be obtained from VI means of basic hydrolysis and subsequent acidification with hydrochloric acid.

Scheme 1

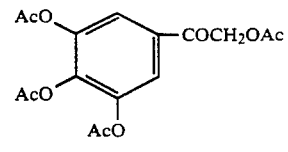

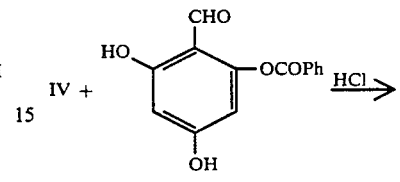

All the known methods, however, are difficult to carry into effect on an industrial scale. Semi-synthesis from natural flavonoid synthons is inconvenient, because of the difficulties of finding the necessary quantities of starting materials in nature, and Robinson's synthesis has drawbacks for reasons of safety. In fact, the preparation of the intermediate IV by the procedure of Scheme 1 requires the use of diazomethane, a reagent with characteristics of toxicity and explosiveness which discourage its use on a large scale.

An object of the present invention is to provide a novel procedure for the preparation of intermediate IV and related compounds which utilizes reactants and operating conditions which are readily transferable to an industrial scale and results in the production of this intermediate in high yields and in a state of high chemical purity.

The process of the invention according to one aspect thereof is based on the realisation that a superior procedure for synthesising delphinidin and its salts involves the synthesis of 3,4,5-trihydroxyacetophenone as an intermediate. As will be described below, 3,4,5-trihydroxyacetophenone can itself be produced by a novel procedure which avoids drawbacks of known processes and can be converted to compound IV in Scheme 1 or related compounds.

According to one aspect of the invention there is provided a process for producing delphinidine which comprises reacting a compound of formula wherein each Pg represents a hydroxyl protecting group and Lg represents a leaving group with a compound of formula

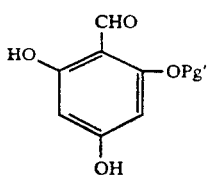

wherein Pg' represents a hydroxyl protecting group characterised in that the compound of formula VII is produced from an intermediate of formula

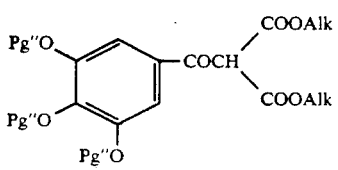

wherein each Pg" represents a hydroxyl protecting group and each Alk represents lower alkyl, by
 (i) subjecting the intermediate of formula IX to hydrolysis and decarboxylation to form 3,4,5-trihydroxyacetophenone of formula

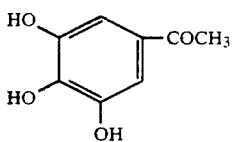

(ii) converting the 3,4,5-trihydroxyacetone to the compound of formula VII by introduction of the protecting groups Pg and converting the group of formula —COCH$_3$ to a group of formula —COCH$_2$Lg.

The compounds of formula IX are novel and form a further aspect of the invention, as do certain novel processes for their production and conversion to 3,4,5-trihydroxyacetophenone.

Thus according to a further aspect of the present invention there is provided a process for producing 3,4,5-trihydroxyacetophenone (X).

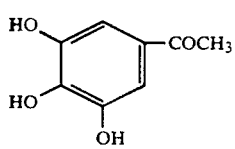

which comprises subjecting a compound of formula

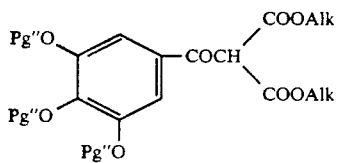

in which each Pg" represents a hydroxyl protecting group and each Alk represents lower alkyl, to hydrolysis and decarboxylation.

The invention further provides a process for producing a compound of formula (IX)

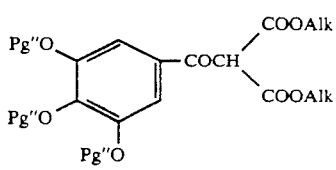

which comprises reacting a compound of formula (XI)

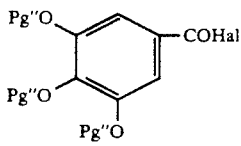

wherein Pg" represents a hydroxyl protecting group and Hal represents halogen, particularly chlorine, with a source of carbanions of formula (XII) derived from a di-loweralkyl malonate

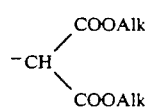

In the above formulae the protecting groups Pg and Pg' and Pg" may be any known protecting group of the hydroxyl function which is stable under the reaction conditions employed, either in producing the intermediate in question or in its subsequent conversion. Thus, for example, the groups Pg, Pg' and Pg" may be a carboxylic acid acyl group derived from, for example, a C$_{1-6}$ aliphatic carboxylic acid, e.g. acetic acid, propionic acid, butyric acid etc or a C$_{6-10}$ aromatic carboxylic acid, e.g. benzoic acid. Alternatively, Pg, Pg' and Pg" may be derived from a sulphonic acid, e.g. toluene sulphonic acid or benzene sulphonic acid.

Preferably, the protecting groups Pg and Pg" are acetyl and the protecting group Pg' is benzoyl. Lg may be any known leaving group, but preferably is a C$_{1-6}$ carboxylic acid acyl group, most preferably acetyl.

Alk may be any straight or branched chain lower alkyl group, but preferably is methyl or ethyl. Hal is preferably chlorine.

The starting material of formula (XI) may be produced by conventional procedures, e.g. by esterifying 3,4,5-trihydroxybenzoic acid so as to introduce protecting groups Pg", followed by reaction of tri-ester

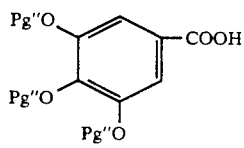

with a halogenating agent, e.g. PCl$_5$ or SOCl$_2$.

The process of the invention may be illustrated by the following Schemes 2 and 3, where Scheme 2 represents the procedures of the invention expressed in terms of general formulae and Scheme 3 represents, by way of example, reactions of specific compounds.

SCHEME 2

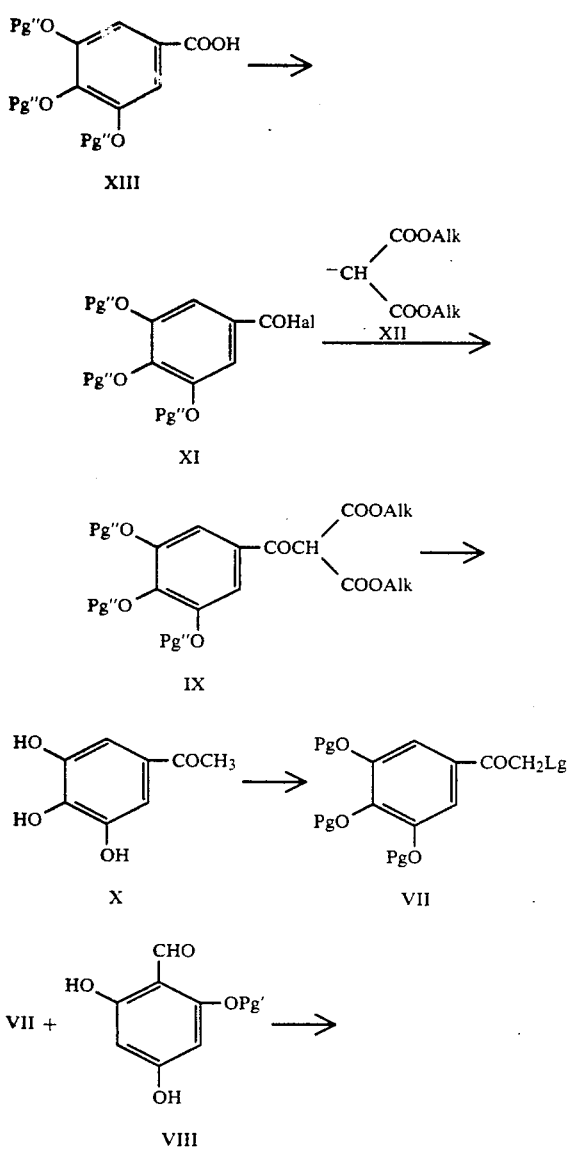

SCHEME 3

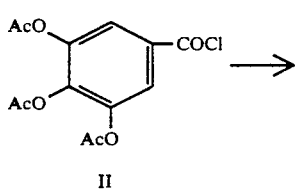

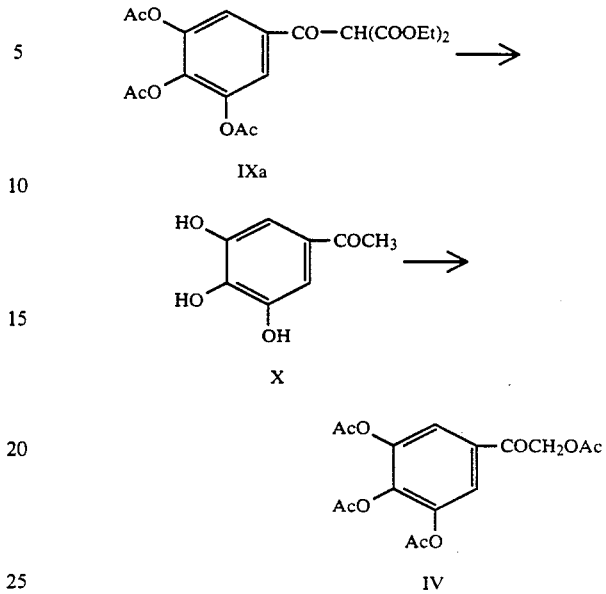

In Scheme 3, the chloride of triacetylgallic acid (II), which may be obtained by known synthesis procedures, may be reacted with ethyl ethoxymagnesium malonate, preparing in situ by reaction between magnesium, ethanol and diethyl malonate, in an aprotic solvent (for example, tetrahydrofuran), to give the novel compound ethyl 3,4,5-triacetoxybenzoylmalonate (IXa). This, which need not necessarily be isolated, is hydrolysed by heating at 70°–100° C. in an acid medium. and, after decarboxylation of the malonic residue, supplies directly the methyl ketone X.

The desired intermediate IV may be obtained from X via a "one pot" synthetic process in which the protection of the phenolic functions as acetates is effected by heating compound X at 30°–50° C. in acetic anhydride containing sulphuric acid as catalyst, ω-bromination and nucleophilic substitution of the bromine with potassium acetate carried out at 90°–110° C.

The product IV can thus be prepared advantageously in only two synthesis operations (XIa→X→IV) without isolation of the intermediate products.

Compared with the method proposed by Robinson, the procedure of the invention, in addition to utilising reactants which are free from danger in use, presents the advantage of enabling intermediate IV to be obtained from starting material II with higher yields (80% instead of 65%) and in a high degree of purity. This last advantage, in fact, is a necessary condition for the preparation of delphinidin chloride free from by-products which cannot be eliminated from the final product by the normal methods of purification.

For the preparation of delphinidin chloride, IV may be condensed with phloroglucinaldehyde which has been suitably protected on the phenolic functions (for example, the 2-O-benzoate V).

After removal of the protecting groups, delphinidin chloride may be obtained in pure form and in high yields (80% from IV), without it being necessary to carry out the laborious purification operations required during Robinson's synthesis.

The following Examples illustrate the invention without limiting it.

EXAMPLE 1

Synthesis of ethyl 3,4,5-triacetoxybenzoylmalonate (IXa)

A suspension of 580 g of magnesium turnings, 100 ml of carbon tetrachloride and 4 l of anhydrous tetrahydrofuran is reacted in an inert atmosphere with 520 ml of absolute ethanol. The reaction mixture is diluted with tetrahydrofuran and a suspension of 3.6 l of diethyl malonate and 860 ml of absolute ethanol is added. When dissolution has taken place, 6.7 kg of the acid chloride of triacetylgallic acid (II) suspended in tetrahydrofuran are added and the reaction mixture is kept at reflux with agitation for one hour. The reaction mixture is diluted with ethyl acetate and with a solution of dilute sulphuric acid.

The organic phase is separated, washed with water, dried and concentrated to a small volume. By dilution of the residue with isopropyl ether, IXa crystallizes and is recovered by filtration and dried.

8.96 kg of IXa are obtained (yield: 96%), m.p. 99°–100° C., M+. at m/z 438.

Found: C, 54.32; H, 5.10%, $C_{20}H_{22}O_{11}$ requires: C, 54.80; H, 5.06%.

EXAMPLE 2

Synthesis of 3,4,5-trihydroxyacetophenone (X) from IXa

A solution of 6.6 kg of IXa in 15 l of acetic acid containing 5 l of 10% sulphuric acid is agitated for three hours at 80° C. The solution is diluted with water, extracted with ethyl acetate and the organic phase is concentrated under vacuum to a small volume until there is incipient crystallisation. Precipitation is completed by cooling, there being obtained 2.33 kg of X (yield: 92%), m.p. 178°–80° C., M+. at m/z 168.

Found: C, 57.00; H, 4.82%, $C_8H_8O_4$ requires: C, 57.11; H, 4.79%.

EXAMPLE 3

Synthesis of 3,4,5-trihydroxyacetophenone (X) from II

The acid chloride of triacetylgallic acid (II, 6.7 kg) is subjected to condensation with diethyl malonate (3.6 l) in the presence of magnesium turnings and ethyl alcohol by the procedure described in Example 1. After extraction with ethyl acetate, the organic phase is evaporated to a small volume, diluted with 20 l of acetic acid containing 6 l of dilute sulphuric acid and kept under agitation at 80° C. for three hours. The mixture is diluted with water, extracted with ethyl acetate and the organic phase is evaporated to dryness. The residue, taken up in 5 l of acetic acid, supplies, after filtration and drying, 3.1 kg (yield: 87%) of X, identical to the product obtained by the procedure described in Example 2.

EXAMPLE 4

Synthesis of ω-acetoxy-3,4,5-triacetoxyacetophenone (IV)

A suspension of 2.1 kg of X in 9 l of acetic anhydride containing 5 ml of concentrated sulphuric acid is heated for two hours under agitation at 50° C. 0.7 l of bromine is added drop-wise and the mixture is allowed to react under agitation for one hour at room temperature. After dilution with 9 l of glacial acetic acid, 3.6 kg of anhydrous potassium acetate are added, heating is carried out under agitation at 100° C. for three hours and the reaction mixture is poured into water/ice. The precipitate is filtered and crystallized from ethyl acetate/cyclohexane. 3.9 kg of IV are obtained (yield: 90%), m.p. 122° C., M+. at m/z 352.

Found: C, 54.32; H, 4.60%, $C_{16}H_{16}O_9$ requires: C, 54.54; H, 4.57%.

EXAMPLE 5

Synthesis of delphinidin chloride (I)

A suspension containing 3.6 kg of phloroglucinaldehyde 2-O-benzoate (V) and 4.6 kg of IV in 50 l of a 2:1 mixture of ethyl acetate and methanol is saturated with gaseous hydrochloric acid under agitation. The mixture is allowed to react to complete dissolution and is kept at rest for 24 hours. The precipitated solid is filtered and suspended under agitation in 40 l of a water-methanol solution containing 2 kg of sodium hydroxide. The reaction mixture is maintained under agitation at 0°–4° C. for 60 minutes and then poured into 30 l of concentrated hydrochloric acid.

The precipitated solid is filtered, washed with dilute hydrochloric acid and recrystallized from methanol-concentrated hydrochloric acid. 3.5 kg of I are obtained (yield: 80%), having a purity not less than 98% determined by means of HPLC analysis.

Found: C, 53.26; H, 3.30; Cl, 10.51%, $C_{15}H_{11}ClO_7$ requires: C, 53.19; H, 3.27; Cl, 10.47%.

We claim:

1. A process for producing delphinidin which comprises reacting a compound of formula

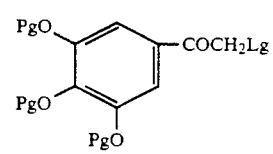

VII wherein each Pg represents a hydroxyl protecting group, and Lg represents an acyloxy group with a compound of formula

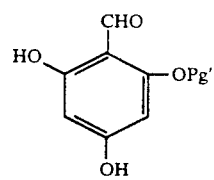

VIII wherein Pg' represents a hydroxyl protecting group characterised in that the compound of formula VII is produced from an intermediate of formula

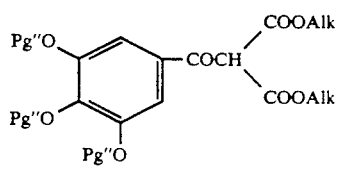

IX wherein each Pg" represents a hydroxyl protecting group and each Alk represents lower alkyl, by
(i) subjecting the intermediate of formula IX to hydrolysis and decarboxylation to form 3,4,5-trihydroxyacetophenone of formula

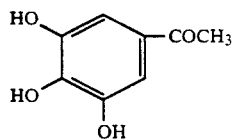

X (ii) converting the 3,4,5-trihydroxyacetophenone to the compound of formula VII by introduction of the protecting groups Pg and converting the group of formula —COCH$_3$ to a group of formula —COCH$_2$Lg.

2. A process according to claim 1 wherein Pg, Pg' and Pg" each represents a carboxylic acid acyl group derived from a C$_{1-6}$ aliphatic carboxylic acid or from a C$_{6-10}$ aromatic carboxylic acid or a radical derived from a sulphonic acid.

3. A process according to claim 1 wherein Pg and Pg" each represents acetyl and Pg' is benzoyl.

4. A process for producing delphinidin which comprises:
(i) reacting 3,4,5-trihydroxyacetophenone with an esterifying reagent capable of converting hydroxyl groups to protected hydroxyl groups to form a compound of formula

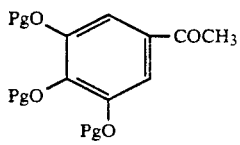

XIV wherein Pg is a hydroxyl protecting group,
(ii) converting the —COCH$_3$ group of the compound of formula XIV to a group of the structure —COCH$_2$Lg wherein Lg is an acyloxy group, by subjecting the compound of formula XIV to ω-bromination to convert said —COCH$_3$ group to a group of structure —COCH$_2$Br and reacting the resulting brominated compound with a nucleophilic reagent capable of introducing the group Lg
(iii) reacting the resulting compound of formula VII

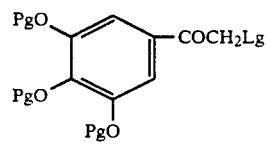

VII with a compound of formula

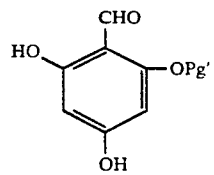

VIII wherein Pg' is a protecting group.
(iv) and hydrolysing the resulting compound of formula

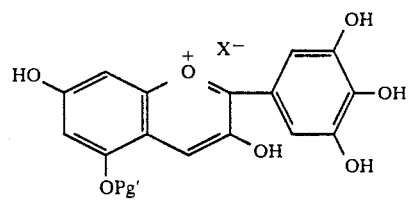

XV wherein Pg' is as defined above and X$^-$ is an anion.

* * * * *